(12) United States Patent
Komuro (10) Patent No.: US 10,149,719 B2
(45) Date of Patent: Dec. 11, 2018

(54) MEDICAL MANIPULATOR

(71) Applicant: OLYMPUS CORPORATION, Tokyo (JP)

(72) Inventor: Takahiro Komuro, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 462 days.

(21) Appl. No.: 14/746,993

(22) Filed: Jun. 23, 2015

(65) Prior Publication Data

US 2015/0282882 A1 Oct. 8, 2015

Related U.S. Application Data

(63) Continuation of application No. PCT/JP2014/052817, filed on Feb. 3, 2014.

(Continued)

(51) Int. Cl.
*A61B 1/00* (2006.01)
*A61B 19/00* (2006.01)
(Continued)

(52) U.S. Cl.
CPC ............ *A61B 19/22* (2013.01); *A61B 1/0016* (2013.01); *A61B 1/00087* (2013.01); *A61B 1/00133* (2013.01); *A61B 1/00135* (2013.01); *A61B 1/00149* (2013.01); *A61B 1/00154* (2013.01); *A61B 1/05* (2013.01); *A61B 17/00234* (2013.01); *A61B 34/30* (2016.02);
(Continued)

(58) Field of Classification Search
CPC .................................................... A61B 1/0125

USPC ................................ 600/104, 106, 113, 114
See application file for complete search history.

(56) References Cited

U.S. PATENT DOCUMENTS 8,864,749 B2 10/2014 Okada
2001/0049509 A1 12/2001 Sekine et al.
(Continued)

FOREIGN PATENT DOCUMENTS

EP 1935354 A2 6/2008
EP 2 294 967 A1 3/2011
(Continued)

OTHER PUBLICATIONS

Extended Supplementary European Search Report dated Aug. 25, 2016 in related European Patent Application No. 14 74 9205.2.
(Continued)

*Primary Examiner* — Alexandra L Newton
*Assistant Examiner* — Rynae Boler
(74) *Attorney, Agent, or Firm* — Scully, Scott, Murphy & Presser, P.C.

(57) ABSTRACT

A medical manipulator including: an elongated main body that is to be inserted into a body; an arm that is provided so as to be protruded forward from a distal end surface of the main body; and an observation part that is located on the distal end surface of the main body and that has an objective optical system for collecting light coming from a front direction, in which the arm and the observation part are relatively movably provided such that the objective optical system is located at a position equivalent to the position of a distal end of the arm or at a position anterior to the distal end of the arm and is located at a position posterior to the distal end of the arm.

12 Claims, 8 Drawing Sheets

Related U.S. Application Data (60) Provisional application No. 61/760,698, filed on Feb. 5, 2013.

(51) Int. Cl.

| | | |
|---|---|---|
| *A61B 1/05* | (2006.01) | |
| *A61B 17/00* | (2006.01) | |
| *A61B 34/00* | (2016.01) | |
| *A61B 34/37* | (2016.01) | |
| *A61B 17/29* | (2006.01) | |
| *A61B 17/34* | (2006.01) | |
| *A61B 34/30* | (2016.01) | |
| *A61B 90/00* | (2016.01) | |

(52) U.S. Cl.
CPC .............. *A61B 34/37* (2016.02); *A61B 34/70* (2016.02); *A61B 90/37* (2016.02); *A61B 2017/00296* (2013.01); *A61B 2017/2906* (2013.01); *A61B 2017/3447* (2013.01); *A61B 2034/301* (2016.02)

(56) References Cited

U.S. PATENT DOCUMENTS

| | | |
|---|---|---|
| 2005/0182292 A1 | 8/2005 | Suzuki |
| 2005/0267335 A1 | 12/2005 | Okada et al. |
| 2006/0149129 A1 | 7/2006 | Watts et al. |
| 2006/0293643 A1* | 12/2006 | Wallace .................. A61B 8/12 606/1 |
| 2007/0249897 A1 | 10/2007 | Miyamoto et al. |
| 2008/0006492 A1 | 1/2008 | Stensson et al. |
| 2008/0051629 A1* | 2/2008 | Sugiyama .......... A61B 1/00193 600/114 |
| 2009/0312645 A1 | 12/2009 | Weitzner et al. |
| 2010/0113873 A1 | 5/2010 | Suzuki et al. |
| 2011/0065985 A1 | 3/2011 | Wehrheim |

FOREIGN PATENT DOCUMENTS

| | | |
|---|---|---|
| EP | 2 430 991 A1 | 3/2012 |
| EP | 1607037 B1 | 2/2015 |
| JP | 2004-141486 A | 5/2004 |
| JP | 2004-180781 A | 7/2004 |
| JP | 2005-334237 A | 12/2005 |
| JP | 2008-289556 A | 12/2008 |
| JP | 2010-000201 A | 1/2010 |
| JP | 2011-525125 A | 9/2011 |
| TW | 200628117 A | 8/2006 |
| WO | WO 2010/053118 A1 | 5/2010 |

OTHER PUBLICATIONS

International Search Report dated May 13, 2014 issued in PCT/JP2014/052817.

* cited by examiner

MEDICAL MANIPULATOR

CROSS-REFERENCE TO RELATED APPLICATIONS

This application is a Continuation Application of International Application PCT/JP2014/052817 filed on Feb. 3, 2014, which claims priority to U.S. Application No. 61/760,698 filed on Feb. 5, 2013.
The Contents of International Application PCT/JP2014/052817 and U.S. Patent application No. 61/760,698 are hereby incorporated by reference herein in its entirety.

TECHNICAL FIELD

The present invention relates to a medical manipulator.

BACKGROUND ART

An endoscope apparatus in which a treatment tool, such as a forceps arm, is attached in a protruded manner in front of an objective lens provided on a distal end surface of an insertion part has been conventionally known (for example, see PTL 1). With this endoscope apparatus, an image of an object, including the forceps arm, is acquired by the objective lens, and treatment is applied while observing the forceps arm and the object at the same time in the image.

CITATION LIST

Patent Literature

PTL 1

The Publication of Japanese Patent No. 4148763

SUMMARY OF INVENTION

Technical Problem

In the endoscope apparatus disclosed in PTL 1, because the forceps arm is located more anterior position to the objective lens, which is provided on the distal end surface of the endoscope insertion part, there is the possibility that, when the insertion part is inserted into the body, the forceps arm forms a blind spot for the objective lens.

The present invention is to provide a medical manipulator capable of enhancing the ease-of-insertion by preventing a blind spot from being formed by an arm.

Solution to Problem

According to an aspect, the present invention is a medical manipulator including: an elongated main body that is to be inserted into a body; an arm that is provided so as to be protruded forward from a distal end surface of the main body; and an observation part that is located on the distal end surface of the main body and that has an objective optical system for collecting light coming from a front direction, in which the arm and the observation part are relatively movably provided such that the objective optical system is located at a position equivalent to the position of a distal end of the arm or at a position anterior to the distal end of the arm and is located at a position posterior to the distal end of the arm.

In the above-described aspect, the observation part may be provided so as to be able to be advanced and retracted in front-back directions.

In the above-described aspect, the arm may be provided so as to be able to be advanced and retracted in front-back directions.

In the above-described aspect, the main body, the arm, and the observation part may be provided with bent portions; and a control section that controls bending states of the bent portions may be provided.

In the above-described aspect, the control section may have a first control mode in which control is performed so that both the bent portions of the arm and the observation part are bent in a cooperative manner in the same direction and with substantially the same curvatures.

In the above-described aspect, the control section may have a second control mode in which control is performed so that all the bent portions of the arm, the observation part, and the main body are bent in an a cooperative in the same direction and with substantially the same curvatures.

In the above-described aspect, the control section may have a third control mode in which control is performed so that the bent portion of the main body is bent in an opposite direction from the bent portions of the arm and the observation part, in a cooperative manner.

DESCRIPTION OF EMBODIMENTS

A medical manipulator 1 according to one embodiment of the present invention will be described below with reference to the drawings.

Figure 1:
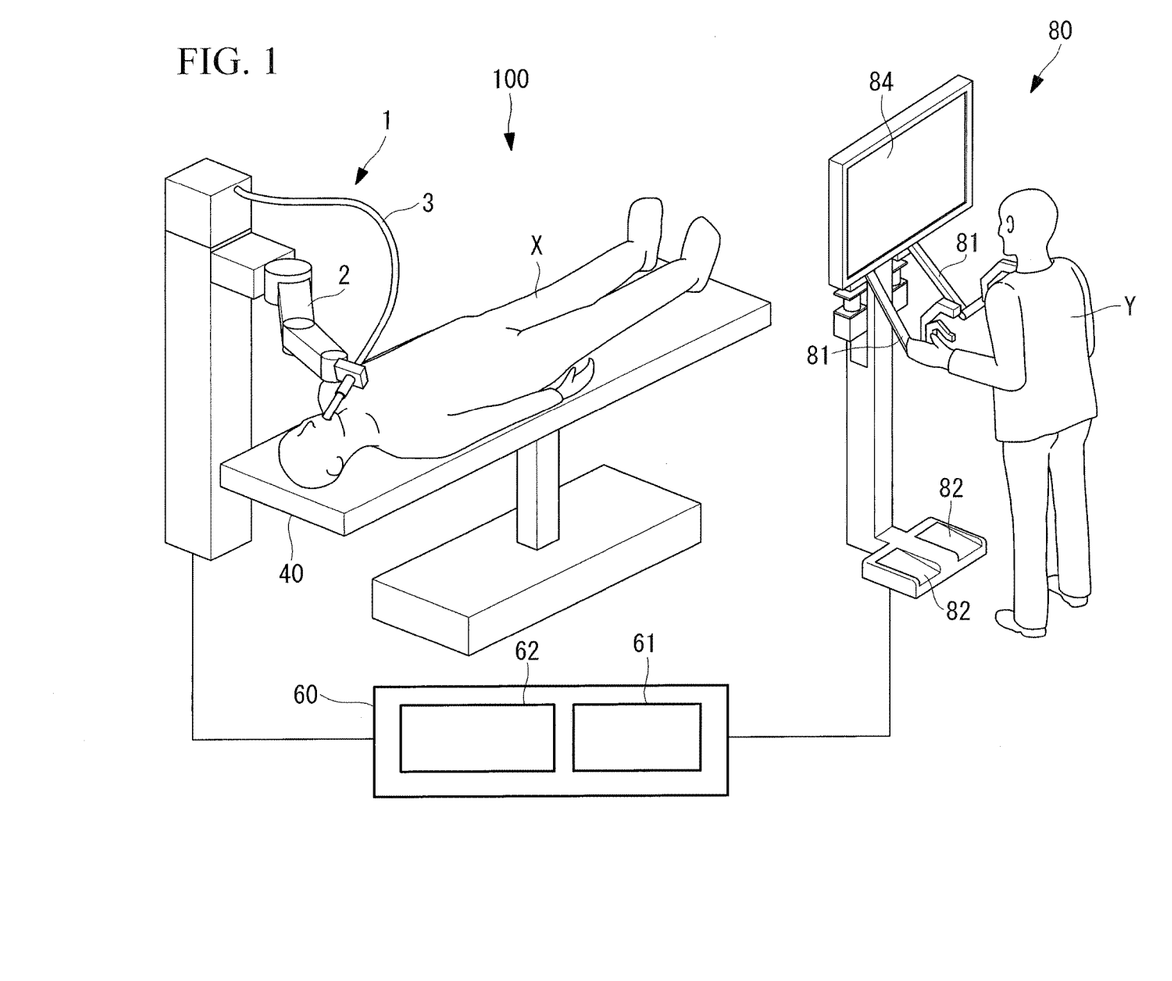
FIG. 1 is an overall configuration diagram showing a surgical manipulator system provided with a medical manipulator according to one embodiment of the present invention.

FIG. 1 is an overall configuration diagram showing, in outline, a surgical manipulator system 100 provided with the medical manipulator 1 according to this embodiment. As shown in FIG. 1, the surgical manipulator system 100 includes the medical manipulator 1 of this embodiment provided in the periphery of a operating table 40 on which a patient X is placed, a control device 60 that is connected to the medical manipulator 1, and a manipulating device 80 with which a manipulation signal for the medical manipulator 1 is input to the control device 60.

As shown in FIG. 1, the medical manipulator 1 includes a slave arm 2 that is driven in the periphery of the operating table 40 and an insertion part 3 that is attached to and handled by the slave arm 2 and whose distal end is to be inserted into a body cavity of the patient X, for example, an oral cavity thereof in the example shown in FIG. 1.

Figure 2:
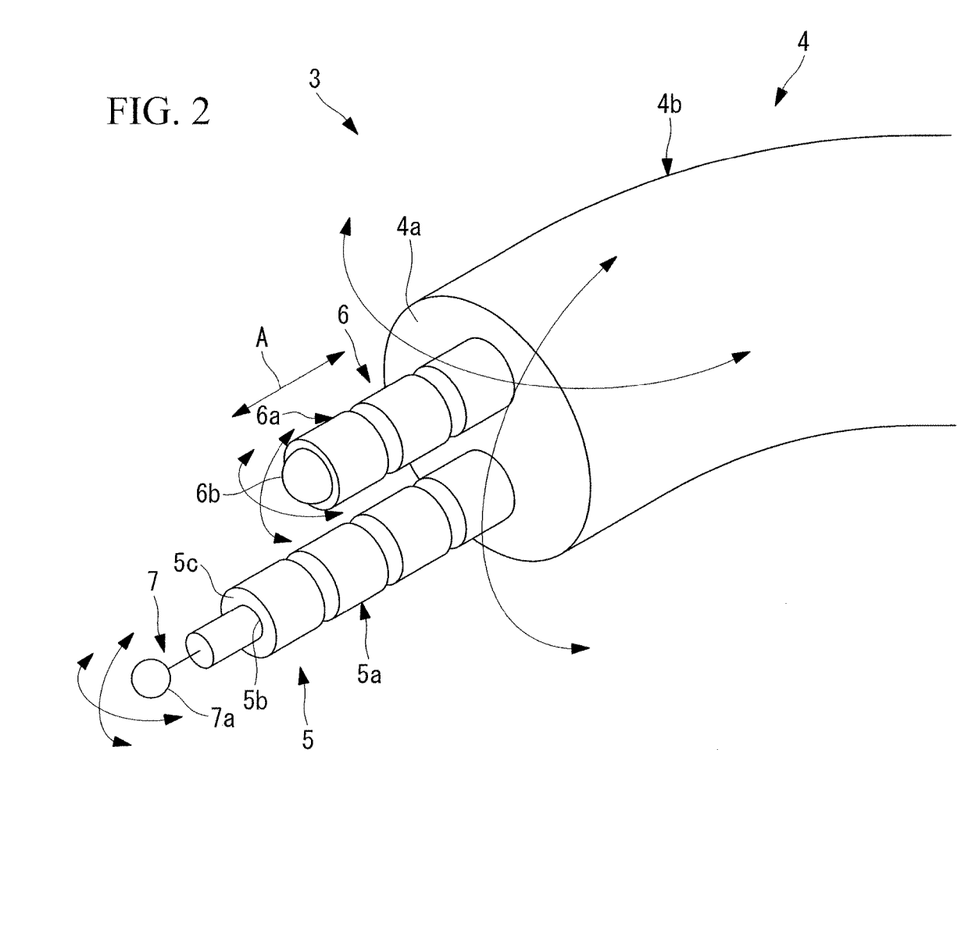
FIG. 2 is a perspective view showing part of a distal end of the medical manipulator shown in FIG. 1.
Figure 3:
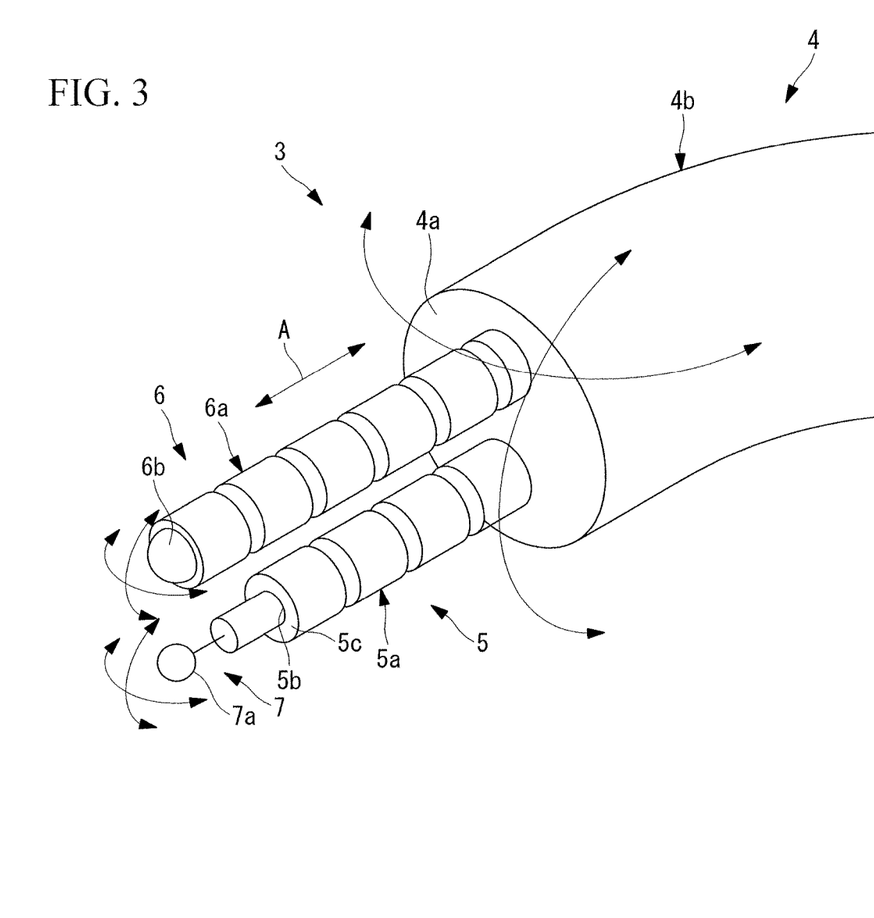
FIG. 3 is a perspective view showing a state in which an observation part provided at the distal end of the medical manipulator shown in FIG. 2 is advanced from the state in FIG. 2.

FIGS. 2 and 3 partially show the distal end of the insertion part 3 of the medical manipulator 1 according to this embodiment.

As shown in FIG. 2, the insertion part 3 includes an elongated main body 4 that has a bent portion 4b near a distal end surface 4a, an arm 5 that is provided so as to be protruded forward from the distal end surface 4a of the main body 4, and an observation part 6 that is protruded forward from the distal end surface 4a of the main body 4. Note that the arm 5 and the observation part 6 are inserted into channels provided in the insertion part 3, for example, and are positioned at a proximal end of the insertion part 3 via holding parts provided in the slave arm 2.

The arm 5 and the observation part 6 also have bent portions 5a and 6a, respectively. The bent portions 4b, 5a, and 6a can change their curvatures by being bent in two directions intersecting the longitudinal axis, over predetermined lengths of the main body 4, the arm 5, and the observation part 6.

The arm 5 has an inner hole 5b passing therethrough over the entire length in the longitudinal direction and allows a treatment tool 7 that is inserted into the inner hole 5b from the proximal end of the main body 4 to be protruded from a distal end 5c of the arm 5. When the bent portion 5a of the arm 5 is bent, the treatment tool 7 is bent accordingly, and the position of a manipulation part 7a, such as forceps, located at the distal end can be fine-tuned.

The observation part 6 has, at a distal end thereof, an objective optical system 6b that collects light coming from an observed site. The observation part 6 is provided so as to be able to be advanced and retracted in the front-back directions with respect to the distal end surface 4a of the main body 4, as indicated by the arrow A. As an advancing and retracting mechanism, an electrically-driven linear-motion mechanism that is provided in the holding part of the slave arm 2 can be used, for example.

With this configuration, when the observation part 6 is advanced with respect to the distal end surface 4a of the main body 4, the objective optical system 6b is located at a position equivalent to the position of a distal end of the treatment tool 7 protruded from the distal end 5c of the arm 5 or a position anterior to the distal end of the treatment tool 7, as shown in FIG. 3, and, when the observation part 6 is retracted, the objective optical system 6b is located a position posterior to the position of the distal end of the treatment tool 7, as shown in FIG. 2.

Figure 4:
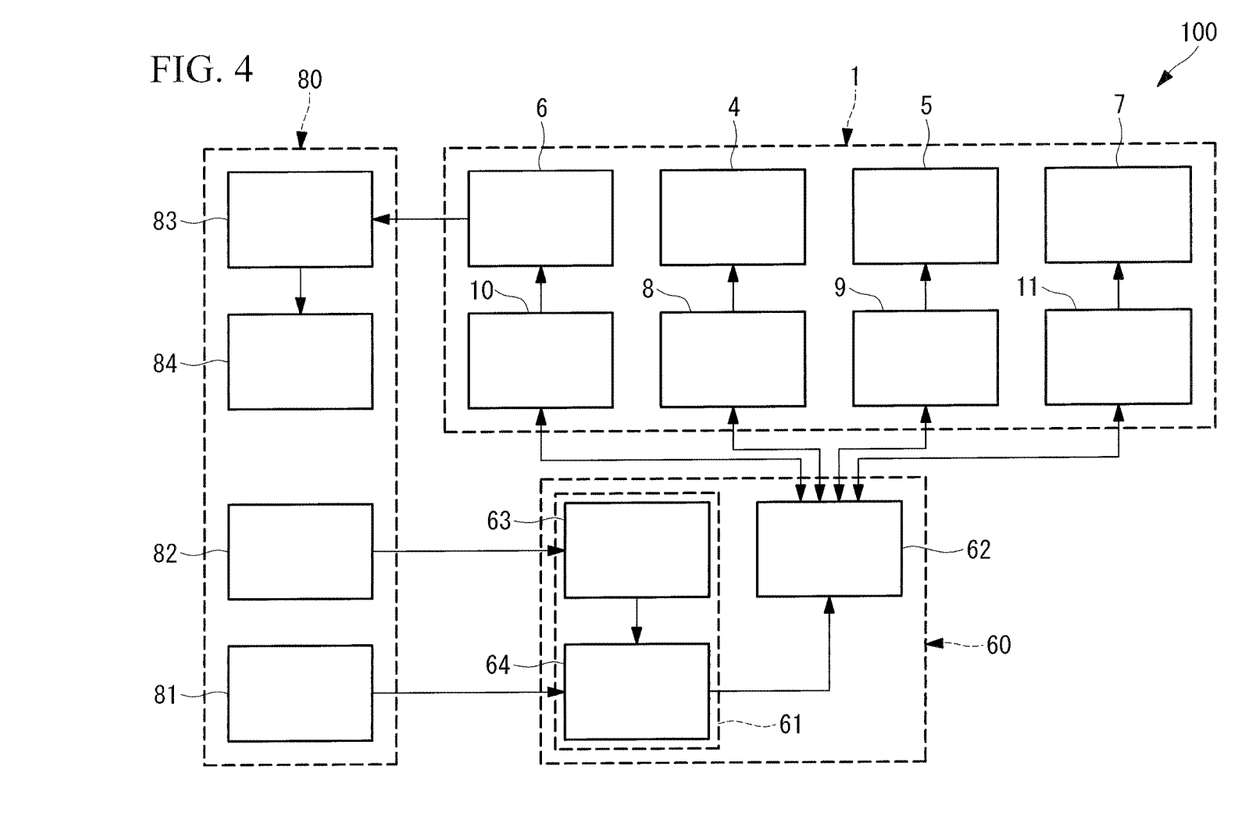
FIG. 4 is a block diagram showing the surgical manipulator system shown in FIG. 1.

As shown in FIG. 4, the main body 4, the arm 5, the observation part 6, and the treatment tool 7 are independently driven by a main-body driving section 8, an arm driving section 9, an observation-portion driving section 10, and a treatment-tool driving section 11, respectively. The slave arm 2 is not shown in FIG. 4.

The manipulating device 80 includes input sections, such as master arms 81 and foot switches 82, to be operated by an operator Y; an image controller 83 for processing an image acquired by the medical manipulator 1; and a display section 84 for displaying the processed image.

The control device 60 includes a master control section 61 and a manipulator control section 62. The master control section 61 includes a mode managing section 63 that is connected to the foot switches 82, which serve as input sections, and an arithmetic section 64 that is connected to the master arms 81 and the mode managing section 63. A manipulation input concerning an operational mode sent from the foot switches 82 is sent to the mode managing section 63, and a signal indicating the selected operational mode is sent from the mode managing section 63 to the arithmetic section 64.

The arithmetic section 64 generates a signal for operating the respective sections of the medical manipulator 1, based on the manipulation input sent from the master arms 81 and the signal indicating the operational mode sent from the mode managing section 63, and sends the generated signal to the manipulator control section 62.

The manipulator control section 62 is connected to the main-body driving section 8, the arm driving section 9, the observation-portion driving section 10, and the treatment-tool driving section 11, and signals sent from detectors (not shown), such as encoders, provided in the driving sections 8 to 11 are fed back to the manipulator control section 62, thus controlling the operations of the sections.

The advantageous effect of the thus-configured medical manipulator 1 according to this embodiment will be described below.

In order to insert the medical manipulator 1 of this embodiment into the body cavity, the operator Y sufficiently protrudes the observation part 6 from the distal end surface 4a of the main body 4, and, as shown in FIG. 3, locates the objective optical system 6b, which is located at the distal end of the observation part 6, at a position equivalent to the position of the distal end of the treatment tool 7 protruded from the distal end 5c of the arm 5 or a position anterior to the distal end of the treatment tool 7.

Therefore, the arm 5 and the treatment tool 7 are not located in the visual field of the observation part 6, thus preventing a blind spot from being formed in part of an observed site by the arm 5 and the treatment tool 7, in an image displayed on the display section 84. As a result, there is the advantage that the operator Y can definitely confirm, on the display section 84, an obstacle existing at the observed site and the forward movement direction of the medical manipulator 1 with respect to the observed site, thus enhancing the ease-of-insertion.

During the insertion of the medical manipulator 1 into the body cavity, if a body-cavity inner wall needs to be grasped with the treatment tool 7, for example, forceps, the operator Y retracts the observation part 6 with respect to the distal end surface 4a of the main body 4 to locate the objective optical system 6b, which is located at the distal end of the observation part 6, closer to a rear end than the treatment tool 7 is, as shown in FIG. 2. Thus, the treatment tool 7 is located within the visual field of the observation part 6, and the body-cavity inner wall can be reliably grasped through accurate manipulation while confirming, on the display section 84, the relative positional relationship between the treatment tool 7 and the body-cavity inner wall and the state of the treatment tool 7. After the body-cavity inner wall is grasped, the observation part 6 is advanced again to locate the objective optical system 6b closer to the front end than the arm 5 and the treatment tool 7 are, thus making it possible to ensure a visual field having no blind spot, which facilitates insertion.

Figure 5:
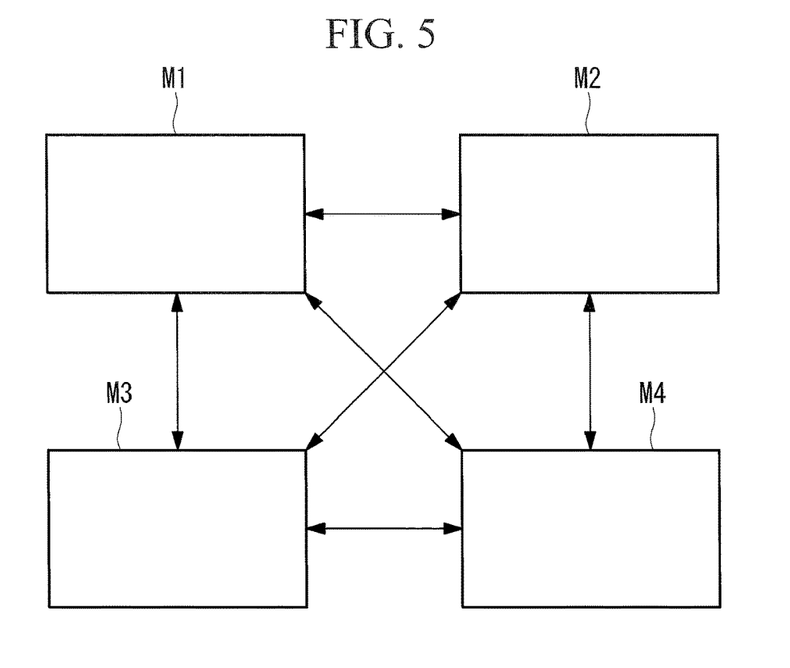
FIG. 5 is a diagram for explaining operational modes of the medical manipulator shown in FIG. 1.

Next, operational modes of the medical manipulator 1 of this embodiment will be described below. As shown in FIG. 5, the medical manipulator 1 has four operational modes, i.e., a standby mode M1, an insertion mode M2, a treatment mode M3, and a removal mode M4. Among the four operational modes, it is possible to directly change from one operational mode to one of the other three operational modes without passing through any other operational modes.

The standby mode M1 is an operational mode in which the insertion part 3 of the medical manipulator 1 is located outside the body of the patient X and stands by.

The treatment mode M3 is an operational mode in which the treatment tool 7 located at the distal end of the insertion part 3 of the medical manipulator 1 reaches an affected area of the patient X and applies treatment to the affected area.

The removal mode M4 is an operational mode in which the insertion part 3 of the medical manipulator 1 is removed from the body of the patient X.

Figure 6:
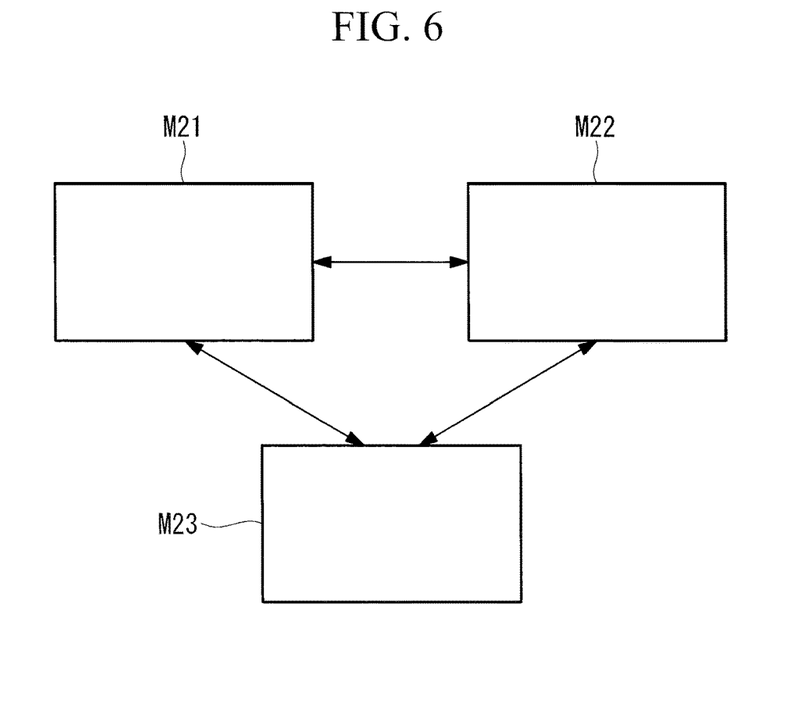
FIG. 6 is a diagram for explaining an insertion mode in the operational modes shown in FIG. 5.

The insertion mode M2 is an operational mode in which the insertion part 3 of the medical manipulator 1 is inserted into the body of the patient X. As shown in FIG. 6, the insertion mode includes three operational modes, i.e., a non-cooperative mode M21, an observation-portion/arm cooperative mode M22, and an observation-portion/arm/main-body cooperative mode M23. Among the three operational modes of the insertion mode M2, it is also possible to directly change from one operational mode to one of the other two operational modes without passing through the rest of the other two operational modes.

Figure 7:
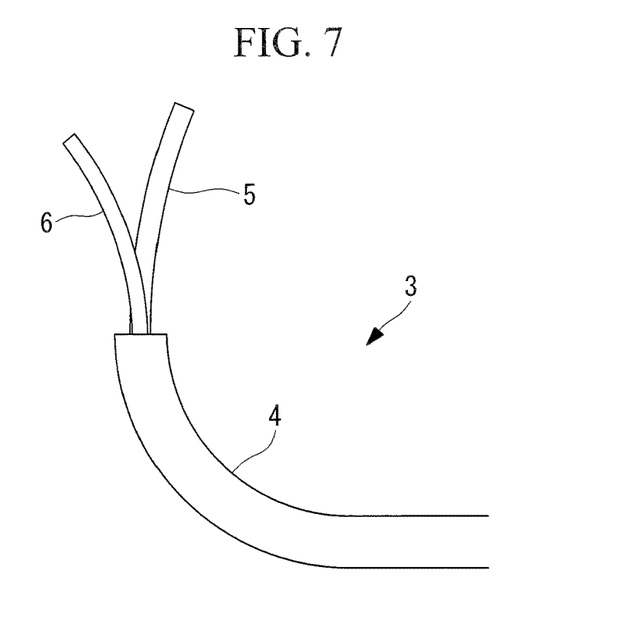
FIG. 7 is a view showing an example case in which the medical manipulator is operated in a non-cooperative mode included in the insertion mode shown in FIG. 6.

In the non-cooperative mode M21, the main body 4, the observation part 6, and the arm 5 can be independently manipulated with the master arms 81, as shown in FIG. 7. In this case, for example, the observation part 6 can be manipulated with the right master arm 81, and the arm 5 and the main body 4 can be manipulated while being switched with the left master arm 81. By doing so, it is possible to observe the state in the body cavity with the observation part 6 and to insert the insertion part 3 while pushing through the body-cavity inner wall with the treatment tool 7, which is located at the distal end of the arm 5.

Figure 8:
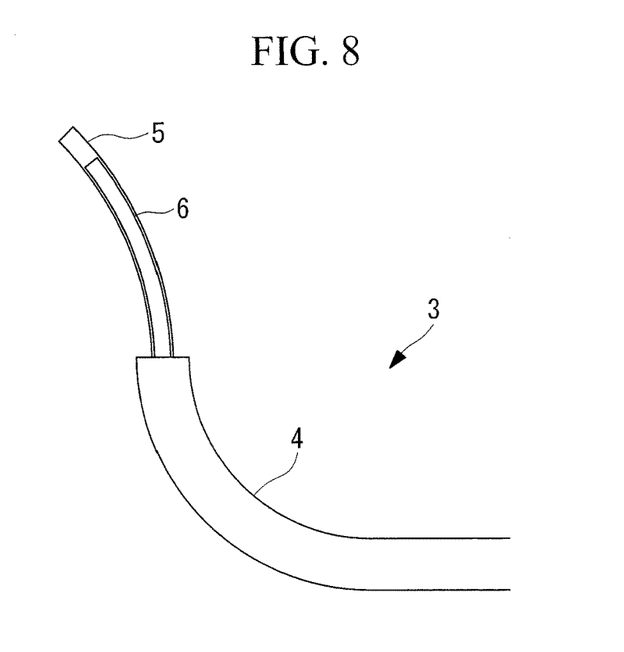
FIG. 8 is a view showing an example case in which the medical manipulator is operated in an observation-portion/arm cooperative mode included in the insertion mode shown in FIG. 6.

The observation-portion/arm cooperative mode M22 is an operational mode in which the observation part 6 and the arm 5 are cooperated and are operated independently of the main body 4, as shown in FIG. 8. In this case, when the observation part 6 is manipulated with the master arm 81, the arm 5 is bent in the same direction and with the same or substantially the same curvature as the observation part 6 and is operated so as to follow the observation part 6. For example, the observation part 6 can be manipulated with the right master arm 81, and the main body 4 can be manipulated with the left master arm 81.

In this operational mode M22, because the observation part 6 and the arm 5 are operated integrally in an cooperative manner, it is possible to manipulate the observation part 6 and the arm 5 in the same way as an integrated endoscope insertion part. Specifically, because the observation part 6 and the arm 5 are operated like a single insertion part, it is possible to enhance the ease-of-insertion in the body and to facilitate the manipulation, compared with a case in which the observation part 6 and the arm 5 are individually manipulated and similarly operated. The main body 4 can be bent independently of the observation part 6 and the arm 5, and the distal end of the insertion part 3 can be wriggled in an S-shaped pattern as a whole. As a result, the medical manipulator 1 can also be applied to a case in which it is inserted into a body cavity having a more-complicated shape.

Figure 9:
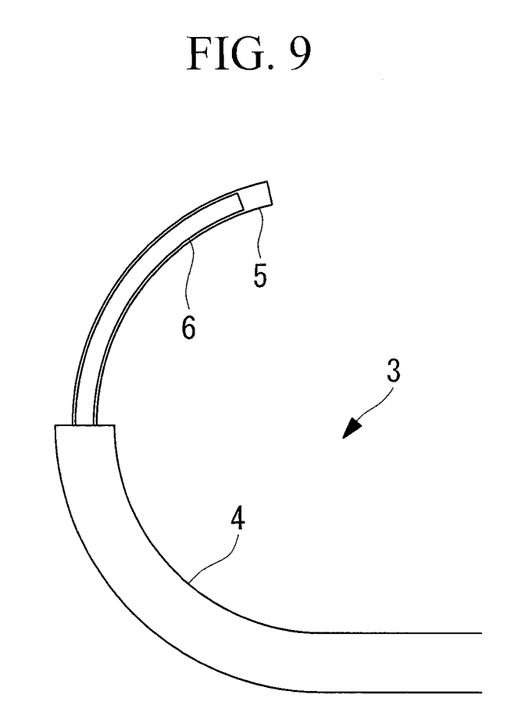
FIG. 9 is a view showing an example case in which the medical manipulator is operated in an observation-portion/arm/main-body cooperative mode included in the insertion mode shown in FIG. 6.

The observation-portion/arm/main-body cooperative mode M23 is an operational mode in which the observation part 6, the arm 5, and the main body 4 are cooperated, as shown in FIG. 9. In this case, when the observation part 6 is manipulated with the master arm 81, the arm 5 and the main body 4 are bent in the same direction and with the same or substantially the same curvatures as the observation part 6 and are operated so as to follow the observation part 6 such that the arm 5 is bent so as to conform to the observation part 6 and such that the main body 4 extends from the proximal end of the observation part 6. For example, the observation part 6, the arm 5 and the main body 4 can all be manipulated merely by manipulating the observation part 6 with the right master arm 81.

In this operational mode M23, because the observation part 6, the arm 5, and the main body 4 are operated like an integrated insertion part 3, they can be manipulated extremely easily, as if a single endoscope insertion part were being manipulated, and enhanced ease-of-insertion can be achieved. Because a relatively hard (rigid) portion is provided at the distal end of the insertion part 3 over a long area from the distal end of the observation part 6 to the proximal end of the main body 4, the force of insertion is easily transferred even in a body cavity that is bent with a large curvature that is located deep inside the body (for example, hepatic flexure), thus enhancing the ease-of-insertion.

Note that, in the medical manipulator 1 according to this embodiment, the arm 5 is fixed to the distal end surface 4a of the main body 4 in a protruded manner, and the observation part 6 is advanced and retracted in the front-back directions, thereby making it possible to locate the objective optical system 6b at a position equivalent to the position of the distal end of the treatment tool 7 in the arm 5 or a position anterior to the distal end of the treatment tool 7 in the arm 5; however, instead of this, it is possible to provide a configuration in which the observation part 6 is fixed to the distal end surface 4a of the main body 4 in a protruded manner, and the arm 5 is advanced and retracted in the front-back directions, thereby making it possible to locate the objective optical system 6b at a position equivalent to the position of the distal end of the treatment tool 7 in the arm 5 or a position anterior to the distal end of the treatment tool 7 in the arm 5.

Alternatively, both the observation part 6 and the arm 5 can be advanced and retracted in the front-back directions, thus locating the objective optical system 6b at a position equivalent to the position of the distal end of the treatment tool 7 in the arm 5 or closer to the front end than the distal end of the treatment tool 7 in the arm 5 is.

In the above-described observation-portion/arm cooperative mode M22, the main body 4 is operated independently; however, instead of this, it is possible not to operate the main body 4 but to leave the main body 4 free, as in a case in which the driving section is not provided. Specifically, only the observation part 6 and the arm 5 may be driven so as to be bent, and the bent portion 4b of the main body 4, which is located near the proximal ends of the observation part 6 and the arm 5, need not be driven so as to be bent. By doing so, at the time of insertion into a bent area of the body cavity that is bent at a sharp angle, the length of the rigid portion is reduced, thus making it possible to enhance the ease-of-insertion.

Figure 10:
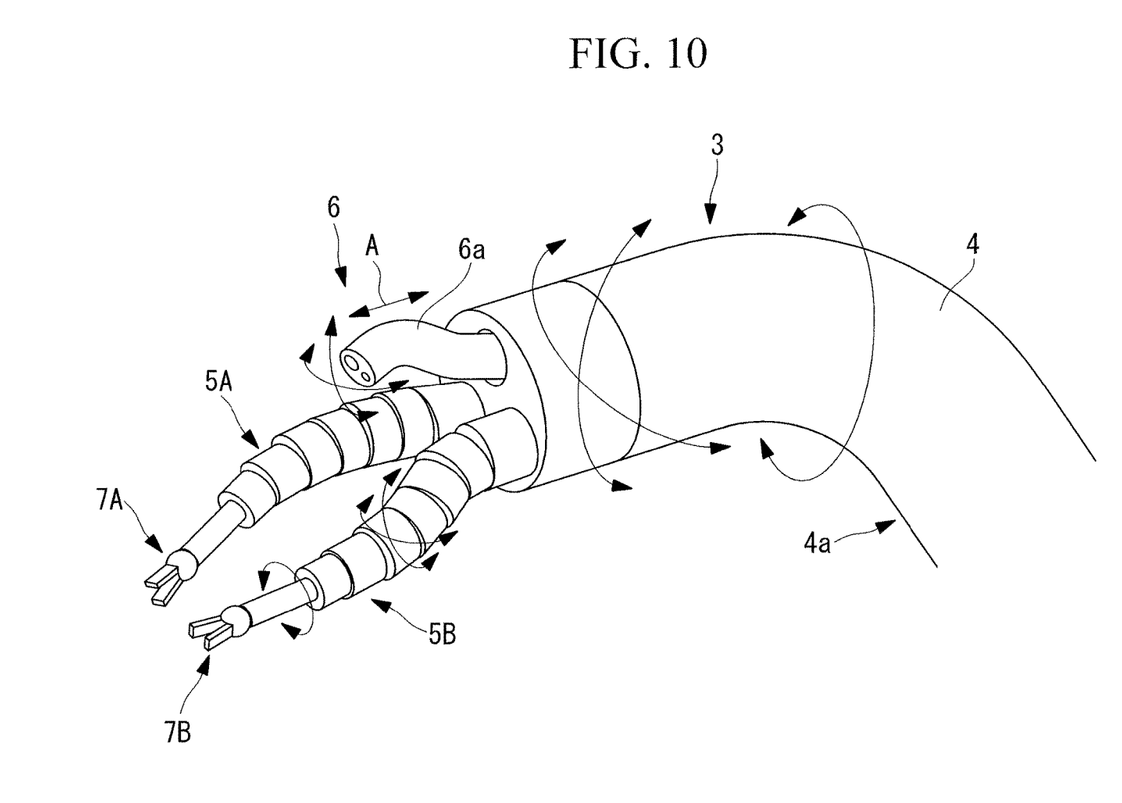
FIG. 10 is a perspective view showing a modification in which the medical manipulator has two arms.

In this embodiment, although an example case in which the single arm 5 is located so as to be protruded forward from the distal end surface 4a of the main body 4 has been described, instead of this, the present invention may be applied to a case in which two arms 5A and 5B or more are provided, as shown in FIG. 10.

In this case, the objective optical system 6b of the observation part 6 is located at a position equivalent to the positions of distal ends of treatment tools 7A and 7B in all the arms 5A and 5B or a position anterior to the distal ends of the treatment tools 7A and 7B in all the arms 5A and 5B, thereby making it possible to prevent a blind spot from being formed by the arms 5A and 5B, thus enhancing the ease-of-insertion.

In the observation-portion/arm cooperative mode M22, all the arms 5A and 5B are cooperated with the observation part 6, thus making it possible to enhance the ease-of-insertion. In the observation-portion/arm/main-body cooperative mode M23, all the arms 5A and 5B, the observation part 6, and the main body 4 are cooperated, thus making it possible to enhance the ease-of-insertion.

In the above-described embodiment, in the observation-portion/arm/main-body cooperative mode M23, the observation part 6, the arm 5, and the main body 4 are bent in an cooperative manner in the same direction and with the same or substantially the same curvatures; however, instead of this, it is possible to bend the observation part 6 and the arm 5 in the opposite direction from the main body 4, so as to form an S-shape as a whole, and to operate them in an cooperative manner.

REFERENCE SIGNS LIST 1 medical manipulator
4 main body
4a distal end surface
4b, 5a, 6a bent portion
5, 5A, 5B arm
6 observation part
6b objective optical system
62 manipulator control section (control section)
M22 observation-portion/arm cooperative mode (first control mode)
M23 observation-portion/arm/main-body cooperative mode (second control mode, third control mode)

The invention claimed is:
1. A medical manipulator system comprising:
a main body configured to be inserted into a subject, wherein the main body extends along a longitudinal axis;
a first arm configured to be protruded distally from a distal end surface of the main body along the longitudinal axis, wherein the first arm comprises:
a treatment tool; and
a first bending mechanism configured to be controlled to bend to change one or more of a position and an orientation of the treatment tool; and
a second arm configured to be protruded distally from the distal end surface of the main body along the longitudinal axis, wherein the second arm comprises:
an objective optical system configured to collect light for forming an image; and
a second bending mechanism configured to be controlled to bend to change one more of a position and an orientation of the objective optical system,
wherein one or both of the first arm and the second arm are configured to move along the longitudinal axis; and a controller configured to:
receive an insertion mode instruction to change control of the first arm and the second arm to an insertion mode:
receive a first arm/second arm cooperation operation mode instruction to change control of the first arm and the second arm to a first arm/second arm cooperative operation mode of the insertion mode; and
in response to receiving the first arm/second arm cooperative operation mode instruction:
receive a single bending instruction for controlling the first bending mechanism and the second bending mechanism cooperatively;
based on the single bending instruction for controlling the first bending mechanism and the second bending mechanism cooperatively, control the first bending mechanism and the second bending mechanism to bend in the same direction and with substantially the same curvature; and
while controlling the first bending mechanism and the second bending mechanism to bend in the same direction and with substantially the same curvature:
receive a protrusion instruction; and
based on the protrusion instruction, control one or both of the first arm and the second arm to move along the longitudinal axis to locate a position of the objective optical system to be equivalent to or anterior to a position of a distal end of the treatment tool.

2. The medical manipulator system according to claim 1, wherein the main body comprises a third bending mechanism configured to be controlled to bend to change one or more of a position and an orientation of the distal end surface of the main body.

3. The medical manipulator system according to claim 2, wherein the controller is configured to:
receive a first arm/second arm/main body cooperation operation mode instruction to change control of the first arm, the second arm and the main body to a first arm/second arm/main body cooperative operation mode of the insertion mode; and
in response to receiving the first arm/second arm/ main body cooperative operation mode instruction:
receive a single bending instruction for controlling the first bending mechanism, the second bending mechanism and the third bending mechanism cooperatively; and
based on the single bending instruction for controlling the first bending mechanism, the second bending mechanism and the third bending mechanism cooperatively, control the first bending mechanism, the second bending mechanism and the third bending mechanism to bend in the same direction and with substantially the same curvature.

4. The medical manipulator system according to claim 2, wherein the controller is configured to:
receive a first arm/second arm/main body cooperation operation mode instruction to change control of the first arm, the second arm and the main body to a first arm/second arm/main body cooperative operation mode of the insertion mode; and
in response to receiving the first arm/second arm/ main body cooperative operation mode instruction:

receive a single bending instruction for controlling the first bending mechanism, the second bending mechanism and the third bending mechanism cooperatively; and based on the single bending instruction for controlling the first bending mechanism, the second bending mechanism and the third bending mechanism cooperatively, control the first bending mechanism and the second bending mechanism to bend in a first direction and with substantially the same curvature, and control the third bending mechanism to bend in a second direction opposite of the first direction.

5. A controller for controlling a medical manipulator comprising:

a main body configured to be inserted into a subject, wherein the main body extends along a longitudinal axis;

a first arm configured to be protruded distally from a distal end surface of the main body along the longitudinal axis, wherein the first arm comprises:
a treatment tool; and
a first bending mechanism configured to be controlled to bend to change one or more of a position and an orientation of the treatment tool; and a second arm configured to be protruded distally from the distal end surface of the main body along the longitudinal axis, wherein the second arm comprises:
an objective optical system configured to collect light for forming an image; and
a second bending mechanism configured to be controlled to bend to change one more of a position and an orientation of the objective optical system,
wherein one or both of the first arm and the second arm are configured to move along the longitudinal axis; and wherein the controller comprises:
a processor comprising hardware, wherein the processor is configured to:
receive an insertion mode instruction to change control of the first arm and the second arm to an insertion mode:
receive a first arm/second arm cooperation operation mode instruction to change control of the first arm and the second arm to a first arm/second arm cooperative operation mode of the insertion mode; and
in response to receiving the first arm/second arm cooperative operation mode instruction:
receive a single bending instruction for controlling the first bending mechanism and the second bending mechanism cooperatively;
based on the single bending instruction for controlling the first bending mechanism and the second bending mechanism cooperatively, control the first bending mechanism and the second bending mechanism to bend in the same direction and with substantially the same curvature; and
while controlling the first bending mechanism and the second bending mechanism to bend in the same direction and with substantially the same curvature:
receive a protrusion instruction; and
based on the protrusion instruction, control one or both of the first arm and the second arm to move along the longitudinal axis to locate a position of the objective optical system to be equivalent to or anterior to a position of a distal end of the treatment tool.

6. The controller according to claim 5,
wherein the main body comprises a third bending mechanism configured to be controlled to bend to change one or more of a position and an orientation of the distal end surface of the main body, and
wherein the processor is configured to control the third bending mechanism.

7. The controller according to claim 6,
wherein the processor is configured to:
receive a first arm/second arm/main body cooperation operation mode instruction to change control of the first arm, the second arm and the main body to a first arm/second arm/main body cooperative operation mode of the insertion mode; and
in response to receiving the first arm/second arm/ main body cooperative operation mode instruction:
receive a single bending instruction for controlling the first bending mechanism, the second bending mechanism and the third bending mechanism cooperatively; and
based on the single bending instruction for controlling the first bending mechanism, the second bending mechanism and the third bending mechanism cooperatively, control the first bending mechanism, the second bending mechanism and the third bending mechanism to bend in the same direction and with substantially the same curvature.

8. The controller according to claim 6,
wherein the processor is configured to:
receive a first arm/second arm/main body cooperation operation mode instruction to change control of the first arm, the second arm and the main body to a first arm/second arm/main body cooperative operation mode of the insertion mode; and
in response to receiving the first arm/second arm/ main body cooperative operation mode instruction:
receive a single bending instruction for controlling the first bending mechanism, the second bending mechanism and the third bending mechanism cooperatively; and
based on the single bending instruction for controlling the first bending mechanism, the second bending mechanism and the third bending mechanism cooperatively, control the first bending mechanism and the second bending mechanism to bend in a first direction and with substantially the same curvature, and control the third bending mechanism to bend in a second direction opposite of the first direction.

9. A non-transitory computer-readable storage medium storing instructions that cause a computer to control a medical manipulator comprising:

a main body configured to be inserted into a subject, wherein the main body extends along a longitudinal axis;

a first arm configured to be protruded distally from a distal end surface of the main body along the longitudinal axis, wherein the first arm comprises:
a treatment tool; and
a first bending mechanism configured to be controlled to bend to change one or more of a position and an orientation of the treatment tool; and a second arm configured to be protruded distally from the distal end surface of the main body along the longitudinal axis, wherein the second arm comprises:

an objective optical system configured to collect light for forming an image; and a second bending mechanism configured to be controlled to bend to change one more of a position and an orientation of the objective optical system, wherein one or both of the first arm and the second arm are configured to move along the longitudinal axis; and wherein the instructions cause the computer to at least perform:

receiving an insertion mode instruction to change control of the first arm and the second arm to an insertion mode:

receiving a first arm/second arm cooperation operation mode instruction to change control of the first arm and the second arm to a first arm/second arm cooperative operation mode of the insertion mode; and in response to receiving the first arm/second arm cooperative operation mode instruction:

receiving a single bending instruction for controlling the first bending mechanism and the second bending mechanism cooperatively;

based on the single bending instruction for controlling the first bending mechanism and the second bending mechanism cooperatively, controlling the first bending mechanism and the second bending mechanism to bend in the same direction and with substantially the same curvature; and while controlling the first bending mechanism and the second bending mechanism to bend in the same direction and with substantially the same curvature:

receiving a protrusion instruction; and based on the protrusion instruction, controlling one or both of the first arm and the second arm to move along the longitudinal axis to locate a position of the objective optical system to be equivalent to or anterior to a position of a distal end of the treatment tool.

10. The non-transitory computer-readable storage medium according to claim 9, wherein the main body comprises a third bending mechanism configured to be controlled to bend to change one or more of a position and an orientation of the distal end surface of the main body, and wherein the instructions cause the computer to control the third bending mechanism.

11. The non-transitory computer-readable storage medium according to claim 10, wherein the instructions cause the computer to at least perform:

receiving a first arm/second arm/main body cooperation operation mode instruction to change control of the first arm, the second arm and the main body to a first arm/second arm/main body cooperative operation mode of the insertion mode; and in response to receiving the first arm/second arm/ main body cooperative operation mode instruction:

receiving a single bending instruction for controlling the first bending mechanism, the second bending mechanism and the third bending mechanism cooperatively; and based on the single bending instruction for controlling the first bending mechanism, the second bending mechanism and the third bending mechanism cooperatively, control the first bending mechanism, the second bending mechanism and the third bending mechanism to bend in the same direction and with substantially the same curvature.

12. The non-transitory computer-readable storage medium according to claim 10, wherein the instructions cause the computer to at least perform:

receiving a first arm/second arm/main body cooperation operation mode instruction to change control of the first arm, the second arm and the main body to a first arm/second arm/main body cooperative operation mode of the insertion mode; and in response to receiving the first arm/second arm/ main body cooperative operation mode instruction:

receiving a single bending instruction for controlling the first bending mechanism, the second bending mechanism and the third bending mechanism cooperatively; and based on the single bending instruction for controlling the first bending mechanism, the second bending mechanism and the third bending mechanism cooperatively, control the first bending mechanism and the second bending mechanism to bend in a first direction and with substantially the same curvature, and control the third bending mechanism to bend in a second direction opposite of the first direction.

* * * * *